United States Patent [19]

Kuhn

[11] Patent Number: 5,520,173

[45] Date of Patent: May 28, 1996

[54] VENTILATION BAG

[75] Inventor: Hans-Joachim Kuhn, Wiesbaden, Germany

[73] Assignee: Heraeus Instruments GmbH, Hanau, Germany

[21] Appl. No.: 354,742

[22] Filed: Dec. 8, 1994

[30] Foreign Application Priority Data

Dec. 8, 1993 [DE] Germany ............... 43 41 746.9

[51] Int. Cl.⁶ ................................................ A61M 16/00
[52] U.S. Cl. ............................ 128/205.13; 128/205.14; 128/205.17; 128/203.12
[58] Field of Search ..................... 128/203.12, 203.28, 128/204.28, 204.18, 205.13, 205.15, 205.17, 206.29, 205.14, 250.14, 250.22; 604/37, 58, 59; 92/90, 91, 92

[56] References Cited

U.S. PATENT DOCUMENTS

| | | | |
|---|---|---|---|
| 3,009,459 | 11/1961 | Ruben | 128/29 |
| 3,046,978 | 7/1962 | Lea | 128/29 |
| 3,262,446 | 7/1966 | Stoner | 128/29 |
| 3,356,100 | 12/1967 | Seeler | 128/205.13 |
| 3,363,833 | 1/1968 | Laerdal | 128/205.13 |
| 3,548,822 | 12/1970 | Seeler et al. | 128/145.7 |
| 4,374,521 | 2/1983 | Nelson et al. | 128/205.13 |
| 4,532,923 | 8/1985 | Flynn | 128/205.13 |
| 4,622,964 | 11/1986 | Flynn | 128/205.24 |

FOREIGN PATENT DOCUMENTS

| | | |
|---|---|---|
| 0616576 | 3/1961 | Canada ............... 128/205.13 |
| 0139363 | 2/1985 | European Pat. Off. . |
| 1183803 | 7/1959 | France . |
| 1872078 | 5/1963 | Germany . |
| 6600376 | 10/1968 | Germany . |
| 1616421 | 8/1969 | Germany . |
| 1934608B2 | 3/1977 | Germany . |
| 8130669 U | 3/1982 | Germany . |
| 0091428B1 | 12/1986 | Germany . |

Primary Examiner—Edgar S. Burr
Assistant Examiner—V. Srivastava
Attorney, Agent, or Firm—Finnegan, Henderson, Farabow, Garrett & Dunner

[57] ABSTRACT

A ventilation bag for a manually operable ventilation device for the artificial ventilation of humans. The bag is made of an elastic, gastight material in the form of an elongated hollow body, with an essentially circular cross section perpendicular to its longitudinal axis with gripping surfaces for differentiated reduction of the volume of the hollow body along its length and having an air inlet opening at one end and an air outlet opening at the other end. To be able to administer different ventilation volumes with relatively greater accuracy and to reduce fatigue to a minimum, the gripping surfaces are arranged, essentially concentrically about the longitudinal axis and one behind the other in the direction of the longitudinal axis, at at least one end of the hollow body, the diameter of the hollow body decreasing toward that at least one end having the gripping surfaces.

10 Claims, 1 Drawing Sheet 5,520,173

VENTILATION BAG

BACKGROUND OF THE INVENTION

This invention relates to a ventilation bag for a manually operable ventilation device for the artificial ventilation of humans. This bag is made of an elastic, air-impermeable material and is in the form of an elongated hollow body having an essentially circular cross section perpendicular to its longitudinal axis. It has external gripping surfaces for differentiated reduction of the volume of the hollow body and an air inlet opening and an air outlet opening. The gripping surfaces are arranged essentially concentric with the longitudinal axis and one behind the other in the direction of the longitudinal axis at at least one end of the hollow body, the diameter of the hollow body decreasing toward the at least one end having the gripping surfaces.

A ventilation bag of this type is known from DE-GM 1 872 078. There, a ventilation bag is described on whose periphery are arranged grooves for accommodating the fingers of the hand. The arrangement of the fingers is fixed by these grooves, and no other finger arrangement is readily possible with this ventilation bag. The ventilation bag is optimally designed for a defined hand size and can only be operated with difficulty by different hand sizes. The grooves for the fingers in this case radiate in relation to the groove for the thumb and form the gripping surfaces of the ventilation bag. A differentiated reduction of the volume of the hollow body is possible only to a very limited extent, because such a differentiation can only be achieved by the operator exerting greater or lesser compression. Thus, the gradation of the volume is at all times carried out subjectively on the part of the operator who has no objective assessment criterion whatsoever available to him or her. However, it is just this objective assessment of the air volume administered that is necessary to rule out injury to the person being ventilated.

A further ventilation bag is known from EP 0 091 428 and German Patent G 81 30 669.5. Here the ventilation bag consists of an elastic and preferably elongated hollow body having an essentially circular cross section, the bag having at each of its longitudinal ends an opening to which an air inlet connector and an air outlet connector, respectively, can be attached. The hollow body has, in its wall, two indentations that extend in the axial direction and are arranged at an angle of approximately 100° to 140° relative to each other in the cross sectional direction of the hollow body. Viewed in cross section, this results in two bag portions which are situated between the indentations, one of which is larger than the other. A person operating the ventilation bag can choose whether to grip the two indentations from the smaller bag portion or from the larger bag portion. In this way the volume of the bag can be reduced to a greater or lesser extent upon compression. The volume of gas delivered via the ventilation bag to the person to be ventilated thus depends on from which side the ventilation bag is gripped. To ventilate a child, for example, the smaller reduction in volume is achieved upon compression. In this way it is possible to take into account the different requirements of people of different sizes during artificial ventilation. However, the reduction in volume achieved in this way is to some extent inexact, because only a small part of the length of the bag is gripped at any one time by the hand of the operator so that the remaining volume is also reduced to a greater or lesser extent by the inherent elasticity of the ventilation bag. In addition, the arrangement of the indentations serving as gripping surfaces is ergonomically unfavorable leading, after prolonged ventilation with the ventilation bag, to the operator showing signs of fatigue.

An object of the present invention, therefore, is to provide a ventilation bag from which different ventilation volumes can be administered with relatively greater accuracy and in which signs of fatigue in the person operating the ventilation bag can be reduced to a minimum.

SUMMARY OF THE INVENTION

According to the invention, this object is achieved by providing a ventilation bag for a manually operable ventilation device for the artificial ventilation of humans, said bag comprising an elongated hollow body made of an elastic, air-impermeable material and having a longitudinal axis and an essentially circular cross section perpendicular to said axis, an inlet opening at one axial end of said body and an outlet opening at the opposite axial end, the diameter of the body decreasing in a stepped manner from a main part toward at least one end thereof to form a plurality of successively reduced diameter gripping surfaces, each surface being essentially concentric with said longitudinal axis, to thereby provide different locations for gripping and compressing the bag with the fingers of the hand for expelling different volumes of air, connecting portions of the hollow body between said gripping surfaces being of concave curvature and increased wall thickness relative to the average wall thickness of the hollow body.

BRIEF DESCRIPTION OF THE DRAWINGS

The invention will be explained below in greater detail with reference to the drawings, which illustrate an embodiment thereof, in which.

DETAILED DESCRIPTION OF THE INVENTION

Figure 1:
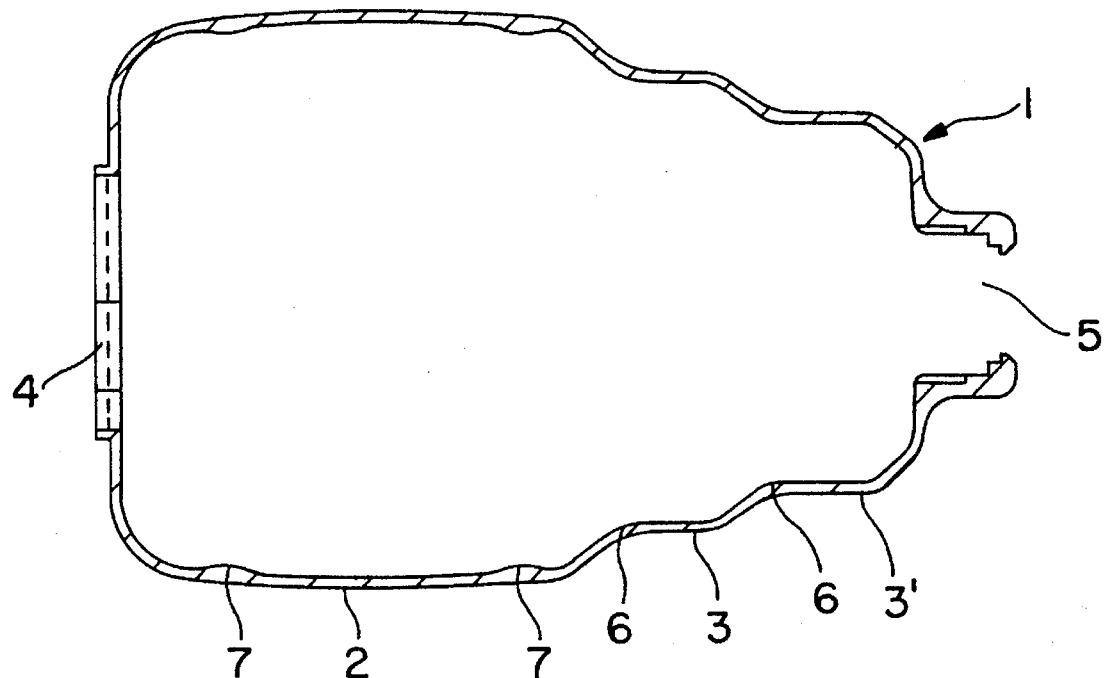
FIG. 1 is a sectional view of a ventilation bag according to the invention.

With reference to the drawings, the ventilation bag is a hollow body 1 made of an elastic material which is to the greatest possible extent airtight, for example of silicone rubber. The hollow body 1 has a cylindrical shape in its main part 2, and the diameter of the hollow body 1 decreases in a stepped manner toward one end, preferably in two steps which form gripping surfaces 3,3'. Main part 2 of the body can also form a further gripping surface 10. The hollow body 1 has an air inlet opening 4 at the end of greater diameter and an air outlet opening 5 at the end of reduced diameter. In practice, the inlet opening 4 is fitted or associated with a one-way valve (not shown) which opens upon expansion and closes upon contraction of the hollow body. Likewise, the outlet opening 5 is fitted or associated with a similar one-way valve (not shown) which opens upon contraction and closes upon expansion of the hollow body 1. Such valves and their operation with the ventilation bag are disclosed in the above-cited DE-GM 1 872 078, EP 0 091 428 and German Patent G 81 30 669.5 and are otherwise well known in the art. Through air outlet opening 5, respiratory air is delivered via the valve associated with that opening to a patient in need thereof.

Figure 2:
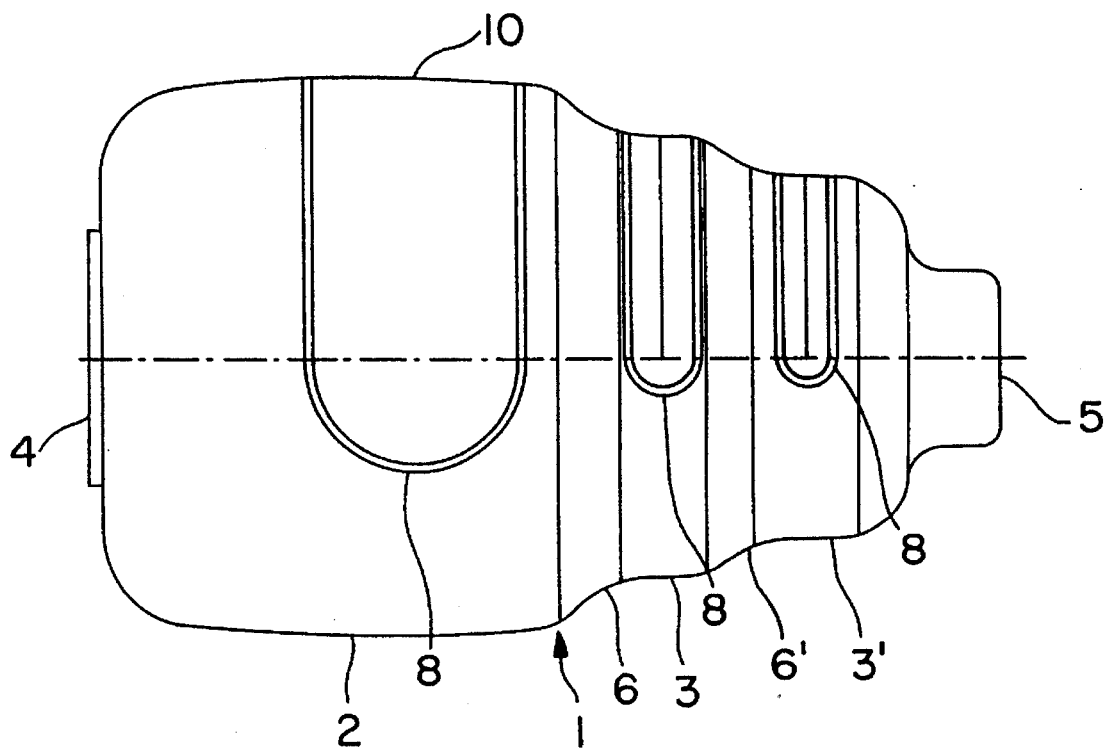
FIG. 2 is a side view of the ventilation bag.

The connecting portions 6, 6' of concave curvature between the two gripping surfaces 3, 3' and between the two gripping surfaces 3, 10 have an increased wall thickness compared to the average wall thickness of the hollow body 1. This increase in wall thickness preferably amounts to approximately 75%. In addition, annular wall reinforcements 7 are located on the inside of the hollow body 1 in the area of cylindrical main part 2, which annular wall reinforcements 7 ensure a reliable self-reexpansion of the ventilation bag following compression of the main part 2. The increase in the wall thickness of the hollow body 1 in the area of this annular reinforcement 7 likewise amounts to approximately 75%. As shown in FIG. 2, the gripping surfaces 3, 3' and 10 are advantageously marked by raised areas 8 to give the operator a clear visual as well as a tactile aid.

With the ventilation bag designed in this way, a differentiated ventilation volume can be achieved by compressing the bag, depending on the gas volume to be administered, either at its gripping surface 10 on main part 2 having the greatest circumference or at one of the gripping surfaces 3, 3' that are arranged on the part of the hollow body having a reduced diameter. Each of the gripping surfaces in this case can be assigned a certain gas volume, so that a number of different air volumes are available corresponding to the number of the gripping surfaces. In addition, the fact that the gripping surfaces for volume-reduced administration of air are arranged at that end of the hollow body reduced in diameter is ergonomically more expedient, with the result that strains in the hand or arm of the operator are largely avoided.

The ventilation bag advantageously has just two steps as shown reducing the diameter of the hollow body, so that a total of three different air volumes can be administered. This number is the one which satisfy most practical requirements.

For a bag design which is relatively simple and can be inexpensively produced, it is advantageous for just one end of the hollow body to have the reduced gripping surfaces. By increasing the thickness of the wall of the hollow body in the areas of concave curvature by at least 25%, and preferably from approximately 50% to 100%, the function of the ventilation bag is influenced in an advantageous manner, both in the accuracy of the volume of air administered and the self-reexpansion of the ventilation bag following compression.

We claim:

1. A ventilation bag for a manually operable ventilation device for the artificial ventilation of humans, said bag comprising an elongated hollow body made of an elastic, air-impermeable material and having a longitudinal axis and an essentially circular cross section perpendicular to said axis, a main part of maximum diameter, an inlet opening at one axial end of said body and an outlet opening at the opposite axial end, the diameter of the body decreasing in a stepped manner from the main part toward at least one end thereof to form a plurality of successively reduced diameter gripping surfaces, each surface being essentially concentric with said longitudinal axis, to thereby provide different locations for gripping and compressing the bag with the fingers of the hand for expelling different volumes of air, connecting portions of the hollow body between said gripping surfaces being of concave curvature and increased wall thickness relative to the average wall thickness of the hollow body.

2. The ventilation bag of claim 1, wherein said hollow body has two reduced diameter gripping surfaces.

3. The ventilation bag of claim 1, wherein the successively reduced diameter gripping surfaces are provided at only one end of the hollow body.

4. The ventilation bag of claim 3, wherein the successively reduced diameter gripping surfaces are provided at said air outlet opening end of the hollow body.

5. The ventilation bag of claim 1, wherein the increase in wall thickness of said connecting portions is at least 25%.

6. The ventilation bag of claim 5, wherein the increase in wall thickness of said connecting portions is from about 50% to 100%.

7. The ventilation bag of claim 1, including raised areas for tactile feel on the outer periphery of the hollow body at said gripping surfaces.

8. The ventilation bag of claim 1, wherein said main part also forms a gripping surface for compressing the bag.

9. A ventilation bag for a manually operable ventilation device for the artificial ventilation of humans, said bag comprising an elongated hollow body made of an elastic, air-impermeable material and having a longitudinal axis and an essentially circular cross section perpendicular to said axis, an air inlet opening at one axial end of said body, an air outlet opening at the opposite axial end, and a main part of maximum diameter adjacent the air inlet opening end of the body and having a gripping surface, the diameter of the body decreasing in a stepped manner from said main part toward said air outlet opening end to form a plurality of successively reduced diameter gripping surfaces, each gripping surface being essentially concentric with said longitudinal axis, to thereby provide different locations for gripping and compressing the bag with the fingers of the hand for expelling different volumes of air, connecting portions of the hollow body between said gripping surfaces being of concave curvature and increased wall thickness relative to the average wall thickness of the hollow body.

10. The ventilation bag of claim 9, wherein said hollow body has three different diameter gripping surfaces.

\* \* \* \* \*